(12) United States Patent
Ingleson et al.

(10) Patent No.: US 7,230,707 B2
(45) Date of Patent: Jun. 12, 2007

(54) SPECTROPHOTOMETER WITH DIGITAL CAMERA

(75) Inventors: Alan Ingleson, Newbury (GB); David Slocum, Yardley, PA (US); Michael H. Brill, Kingston, NJ (US)

(73) Assignee: Datacolor Holding AG, Lucerne (CH)

( * ) Notice: Subject to any disclaimer, the term of this patent is extended or adjusted under 35 U.S.C. 154(b) by 73 days.

(21) Appl. No.: 11/016,033

(22) Filed: Dec. 17, 2004

(65) Prior Publication Data

US 2005/0134853 A1    Jun. 23, 2005

Related U.S. Application Data

(60) Provisional application No. 60/531,530, filed on Dec. 19, 2003.

(51) Int. Cl.
*G01J 3/46* (2006.01)
(52) U.S. Cl. ..................................... 356/402
(58) Field of Classification Search ................ 356/402, 356/446
See application file for complete search history.

(56) References Cited

U.S. PATENT DOCUMENTS

| | | | | |
|---|---|---|---|---|
| 4,785,336 A | * | 11/1988 | McComb et al. | 356/445 |
| 5,754,283 A | * | 5/1998 | Keane et al. | 356/445 |
| 6,147,749 A | * | 11/2000 | Kubo et al. | 356/436 |
| 6,362,888 B1 | * | 3/2002 | Jung et al. | 356/419 |
| 6,545,240 B2 | * | 4/2003 | Kumar | 356/318 |
| 6,614,530 B1 | * | 9/2003 | Duez et al. | 356/406 |
| 6,721,048 B2 | * | 4/2004 | Yokota et al. | 356/319 |
| 2002/0185609 A1 | * | 12/2002 | Giering | 250/458.1 |
| 2003/0052280 A1 | * | 3/2003 | Foster et al. | 250/458.1 |

OTHER PUBLICATIONS

PCT Search Report, mail date Jun. 20, 2006, pp. 1-5.

* cited by examiner

*Primary Examiner*—Layla G. Lauchman
*Assistant Examiner*—Kara Geisel
(74) *Attorney, Agent, or Firm*—Kin-Wah Tong, Esq.; Patterson & Sheridan, LLP

(57) ABSTRACT

Systems, methodologies, media, and other embodiments associated with color measuring are described. One exemplary system embodiment includes a spectrophotometer, one or more light sources for illuminating an interior of the spectrophotometer, and a digital camera configured at a port of the spectrophotometer and being configured to measure light components from a sample. In the present invention, segmentation logic is provided for the spectrophotometer that is configured to employ computational image segmentation to characterize specular reflection from a sample and to characterize a selected patch or portion from the test sample, such as a selected color in a multicolor pattern. In accordance with the present invention, the spectrophotometer and the included digital camera may be color-characterized in situ.

22 Claims, 5 Drawing Sheets

SPECTROPHOTOMETER WITH DIGITAL CAMERA

CROSS-REFERENCE TO RELATED APPLICATIONS

This application claims benefit of U.S. Provisional Patent Application Ser. No. 60/531,530, filed Dec. 19, 2003, which is herein incorporated by reference in its entirety.

BACKGROUND OF THE INVENTION

1. Field of the Invention

The present invention generally relates to color measuring devices and more specifically to systems, methods, computer-readable media, and other devices associated with measuring of color of a sample under test using a spectrophotometer or other color measuring device.

2. Description of the Related Art

A specular (mirror-path, or gloss) component of light reflecting from a material sample is often different in color from the body-reflection (perhaps matte) component. For example, in dielectric materials, the specularly-reflected light has the same relative spectrum as that of the incident illumination. Characterizing the color of a sample through a spectrophotometer (for example, an instrument based on an integrating sphere) can be designed to separate the specular from the matte component of reflection. That task is not difficult for smooth samples: Standard practice with integrating spheres simply uses a closable port that excludes or includes the light within a small incidence angle of the mirror path to the exit port of the device (the port through which the reflected light is recorded by the spectrophotometer). However, for rough samples (and particularly for textiles) such practice does not truly separate out the specular component: The specular reflection arises from elsewhere on the sphere than the specular port. Characterizing the geometry of the specular component of reflection through means other than the simple opening or closing of a hole in the integrating sphere may be useful.

A user may wish to measure the reflectance properties of a sample of material in an industrial "batch" and compare those properties with a standard sample. The "batch" may incorporate the material in a pattern (e.g., a textile pattern), whereas the standard is ensured to be calorimetrically uniform over its entire surface. A spectrophotometer can give accurate reflectance values for a sample that is spatially uniform (such as a calibrating tile). However, it is difficult to measure the reflectance spectrum of a part of a patterned material. The sample port of the spectrophotometer must be sized and shaped specifically for the part of the material specimen that is to be measured. Such adaptation may produce its own artifacts of measurement (e.g., depth of the mask next to the small area reduces the illumination to that area).

An integrating-sphere spectrophotometer can have several automatic mechanisms that determine the aperture of the sample port, whether the sample port door is open or closed, and the position of the sample. All these mechanisms are quite expensive in current implementations. Also, the spectrophotometer by itself does not allow viewing and adjustment of the sample once the sample is readied for measurement.

SUMMARY OF THE INVENTION

Color measuring systems, methods, computer-readable media, graphical user interfaces, and other embodiments associated with color measuring are provided herein. In one embodiment of the present invention, a color measuring system includes an integrating-sphere spectrophotometer combined with a camera that may be color-characterized in situ. The spectrophotometer includes a calibrated and/or color-characterized video camera configured to measure quantitatively such image characteristics as the specular component of a sample's reflectance, the reflectance of a small, selected part of a variegated pattern from the sample, and other color characterization functions.

In an alternate embodiment of the present invention, a spectrophotometer is provided that is configured with a digital camera and one or more secondary light sources configured to color-characterize the camera with standard material samples/test samples in situ. In the present invention, segmentation logic is provided for the spectrophotometer that is configured to employ computational image segmentation to characterize specular reflection from a uniform sample and to characterize a selected patch or portion from the test sample, such as a selected color in a multicolor pattern. In one embodiment of the present invention, the segmentation logic is implemented as software and is provided on any desired computer-readable medium. The segmentation logic may be part of the processing system of the spectrophotometer and/or may be part of a computing device operably connected to the spectrophotometer.

In an embodiment of a color measuring system of the present invention implemented for measuring a sample having a non-uniform pattern, image segmentation logic may be configured to automatically segment the camera image into uniformly colored areas, which may be separately characterized. The image segmentation logic associated with the camera may also be used to determine the state of opening of a sample port, the aperture of the port, and the position of the sample.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. Furthermore, elements may not be drawn to scale.

To facilitate understanding, identical reference numerals have been used, where possible, to designate identical elements that are common to the figures.

DETAILED DESCRIPTION

Figure 1:
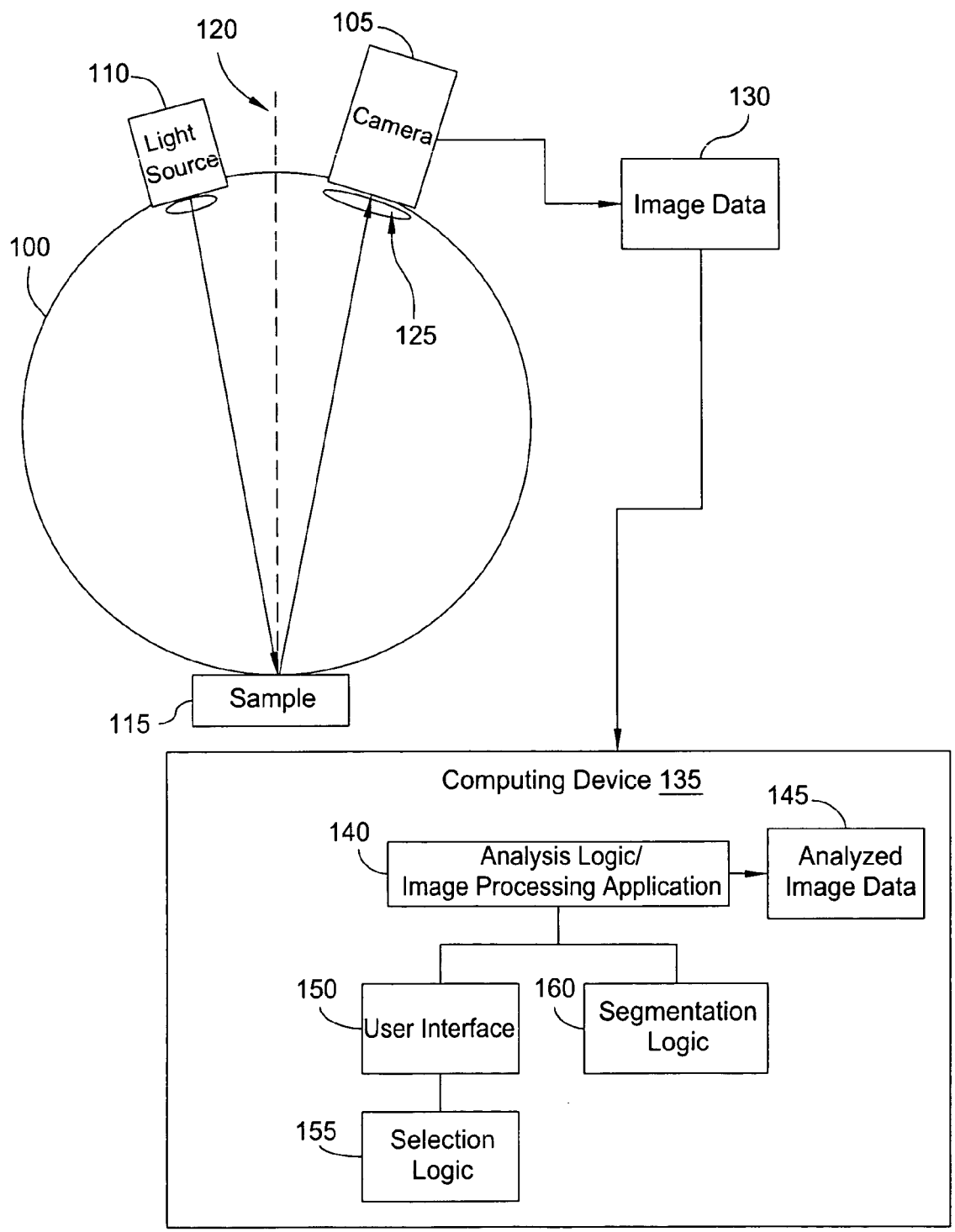
FIG. 1 depicts a high level block diagram of a color measuring system in accordance with an embodiment the present invention.

"Logic", as used herein, includes but is not limited to hardware, firmware, software and/or combinations of each to perform a function(s) or an action(s), and/or to cause a function or action from another logic, method, and/or system. For example, based on a desired application or need, logic may include a software controlled microprocessor, discrete logic like an application specific integrated circuit (ASIC), a programmed logic device, a memory device containing instructions, or the like. Logic may include one or more gates, combinations of gates, or other circuit components. Logic may also be fully embodied as software. Where multiple logical logics are described, it may be possible to incorporate the multiple logical logics into one physical logic. Similarly, where a single logical logic is described, it may be possible to distribute that single logical logic between multiple physical logics.

An "operable connection", or a connection by which entities are "operably connected", is one in which signals, physical communications, and/or logical communications may be sent and/or received. Typically, an operable connection includes a physical interface, an electrical interface, and/or a data interface, but it is to be noted that an operable connection may include differing combinations of these or other types of connections sufficient to allow operable control. For example, two entities can be operably connected by being able to communicate signals to each other directly or through one or more intermediate entities like a processor, operating system, a logic, software, or other entity. Logical and/or physical communication channels can be used to create an operable connection.

"Signal", as used herein, includes but is not limited to one or more electrical or optical signals, analog or digital signals, data, one or more computer or processor instructions, messages, a bit or bit stream, or other means that can be received, transmitted and/or detected.

"Software", as used herein, includes but is not limited to, one or more computer or processor instructions that can be read, interpreted, compiled, and/or executed and that cause a computer, processor, or other electronic device to perform functions, actions and/or behave in a desired manner. The instructions may be embodied in various forms like routines, algorithms, modules, methods, threads, and/or programs including separate applications or code from dynamically linked libraries. Software may also be implemented in a variety of executable and/or loadable forms including, but not limited to, a stand-alone program, a function call (local and/or remote), a servelet, an applet, instructions stored in a memory, part of an operating system or other types of executable instructions. It will be appreciated by one of ordinary skill in the art that the form of software may be dependent on, for example, requirements of a desired application, the environment in which it runs, and/or the desires of a designer/programmer or the like. It will also be appreciated that computer-readable and/or executable instructions can be located in one logic and/or distributed between two or more communicating, co-operating, and/or parallel processing logics and thus can be loaded and/or executed in serial, parallel, massively parallel and other manners.

Suitable software for implementing the various components of the example systems and methods described herein include programming languages and tools like Java, Pascal, C#, C++, C, CGI, Perl, SQL, APIs, SDKs, assembly, firmware, microcode, and/or other languages and tools. Software, whether an entire system or a component of a system, may be embodied as an article of manufacture and maintained or provided as part of a computer-readable medium as defined previously. Another form of the software may include signals that transmit program code of the software to a recipient over a network or other communication medium. Thus, in one example, a computer-readable medium has a form of signals that represent the software/firmware as it is downloaded from a web server to a user. In another example, the computer-readable medium has a form of the software/firmware as it is maintained on the web server. Other forms may also be used.

FIG. 1 depicts a high level block diagram of a color measuring system in accordance with an embodiment the present invention. The color measuring system of FIG. 1 illustratively comprises an integrating-sphere spectrophotometer 100 operably connected to a multi-segment detector (illustratively a camera) 105. The color measuring system of FIG. 1 further comprises a light source 110, a sample 115, a specular port 125 of the integrating-sphere spectrophotometer 100 and a computing device 135. For simplicity, other components such as additional light sources, baffles, ports, sensors, and the like are not shown in the integrating-sphere spectrophotometer 100 but will be readily understood by those skilled in the art as being available features. One example of a color measuring device can be as described in pending U.S. Provisional Patent Application Ser. No. 60/450,311, filed Feb. 27, 2003, title "Spectrophotometer Color Measurement and Diagnostics Over the Web" which is incorporated herein by reference in its entirety. The camera 105 can be for example, a digital camera, a video camera, a CCD camera, other types of cameras, and/or combinations of these, that is capable of observing and providing signal data that represents color from a sample object under test. The camera 105 can be an independently operable device like a standard digital camera.

In one embodiment, a light source 110 is used to illuminate the sample 115 positioned in a sample port (not shown) of the integrating sphere spectrophotometer 100. The camera 105 is positioned to receive reflected light from the sample 115 from an opposite angle from a normal 120 to the sample as the light source 110 (e.g. at the specular angle). A specular port 125 that can open or close is located on the integrating-sphere spectrophotometer 100 in front of the described location of the camera in order to control specular reflection. The camera 105 is operably connected by being mounted to the sphere 100 at the specular port 125, mounted adjacent to the port 125, or mounted outside the sphere 100 but configured to receive light from the port 125.

The camera 105 is configured to measure light properties from the sample 115. For example, the camera 105 may be color characterized and used to measure a reflected component (e.g. gloss component) from the sample 115. The camera 105 is configured to generate image data 130 in the form of signals representing the received light. In various embodiments, the camera 105 may include data transceiver logic and one or more communication ports that can establish a communication link/computer communication with the computing device 135 (e.g. wireless, wired, or other) to which the image data 130 may be transmitted. In one embodiment of the present invention, the camera 105 may be Bluetooth enabled with a Bluetooth compatible transceiver and appropriate communication protocol logic. In this configuration, the camera 105 may transmit the image data 130 to another Bluetooth enabled device such as the computing device 135. The image data 130 may then be processed by the computing device 135.

In the embodiment of FIG. 1, the computing device 135 comprises an analysis logic block 140 that, in one embodiment, may be an image processing application embodied in software. The computing device 135 of FIG. 1 further comprises a user interface 150, a segmentation logic block and a selection logic block 155. The analysis logic 140 is configured to receive the image data 130, process the data in any desired way, and provide results of the analysis, such as color information, characteristics, or other properties of the sample 115. The output may be configured in any desired signal form such as analyzed image data 145. Thus, with the camera 105 positioned in at the specular port 125 and with the image processing application 140, the system is able to characterize a geometry and magnitude of the specular component of the sample's reflection based on the measured values from the camera 105.

In one embodiment of the present invention, the analysis logic 140 is configured to allow a user to dynamically select a portion of the image data 130 in real-time and the selected portion is analyzed for color information. For example, suppose the sample 115 includes a multi-color pattern like plaid. The camera 105 may generate an image or picture of the sample 115 and communicate the picture as the image data 130 to the computing device 135 for processing. Analysis of the image data 130 as a whole, in this case, would probably not provide useful color information because the multiple colors would cause the analysis to provide an average color value of all colors. However, an analysis of individual colors from the sample may be desired to determine specific color data.

The analysis logic 140 is configured with a graphical user interface 150 that allows a user to view the image data 130 (e.g. the picture of the sample) and to select a region of interest for analysis, and/or other image processing options. For example in one embodiment of the present invention, the graphical user interface 150 may be implemented in software and configured to cause the computing device 135 to display the image data 130 on a display (not shown). Logic operations of the present invention are configured to allow a user to make selections, input data, request data, and otherwise interact with the image data 130, the analysis logic 140, and/or other component of the computing device 135.

The selection logic 155 of the computing device 135 of FIG. 1 is configured to enable the user to select a region of interest from the image for color analysis or other processing. The region of interest may be selected pixels or an area that corresponds to an individual color from the multicolor sample. An input device such as a mouse, pointer, or the like may be configured to allow a user to select the region of interest. The pixel information associated with the selected region is then analyzed individually and separately from the rest of the image data 130 to provide color information for the selected region. For example, the segmentation logic 160 of the computing device 135 of FIG. 1 is provided to segment the image data 130 based on the selected region of interest and pull out the corresponding pixel information for analysis. By repeating this process for other areas having different colors in the multicolor sample, individual color information (e.g. pixel color values) may be obtained for each different color. Although the color measuring system of FIG. 1 depicts a camera for measuring light properties of an illuminated sample, it will be appreciated by those skilled in the art and informed by the teachings of the present invention, that other light measuring devices, such as a group of photodiodes, photodetectors, and/or other light detecting instruments, may be used in place of the camera depicted in the color measuring system of FIG. 1.

Figure 2:
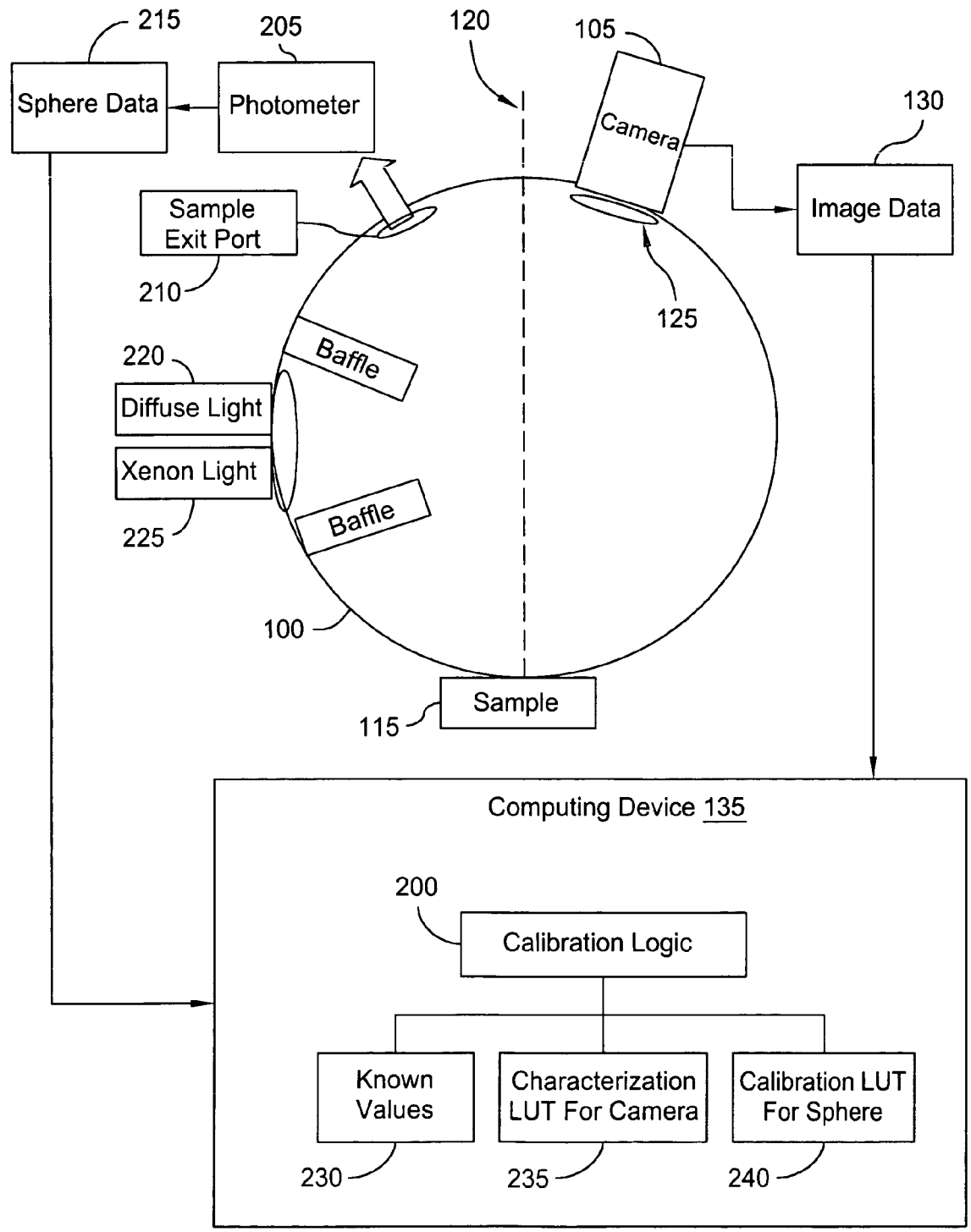
FIG. 2 depicts a high level block diagram of a second color measuring system in accordance with an alternate embodiment of the present invention.

FIG. 2 depicts a high level block diagram of a second color measuring system in accordance with an alternate embodiment of the present invention. The measuring system of FIG. 2 is another example of a color measuring system of the present invention including a calibration system for the integrating-sphere spectrophotometer 100 and the camera 105. In the color measuring system of FIG. 2, a calibration/characterization logic 200 is provided in the computing device 135 to perform color calibration/characterization for the integrating-sphere spectrophotometer 100, for the camera 105, or for both. In FIG. 2, the integrating-sphere spectrophotometer 100 is depicted with a photometer 205 that is configured to detect light from a sample exit port 210. The photometer 205 may include, for example, one or more photodetectors, photodiodes, photomultiplier tubes, and/or other type of optical radiation detecting device. Signals representing the detected light are transmitted to the computing device 135 as sphere data 215. The integrating-sphere spectrophotometer 100 also includes a diffuse light source 220 and a flash light source 225, such as a Xenon light. In the embodiment of the present invention of FIG. 2, the light sources 220 and 225 are positioned at the same port in the integrating-sphere spectrophotometer 100. One or more baffles (not shown) may be used to block a direct illumination path from the light sources 220, 225 to the sample 115, the camera 105, and/or the photometer 205.

Using a set of color samples (e.g. color tiles) having known color values 230, each color tile may be placed as the sample 115 and measured with the sphere/camera combination in, for example, two calibration modes. A first calibration mode is used to characterize the camera 105 by illuminating the diffuse light 220 and measuring/reading image signals with the camera 105 corresponding to the sample 115. The image signals are communicated to the computing device 135 as image data 130. The measured value (e.g. image data 130) for each color tile is then compared to its corresponding known value 230 and a characterization offset is determined for that value. Repeating this described procedure for multiple color tiles provides additional characterization offset values and a characterization table, such as a characterization look up table (LUT) 235, may generated for the camera 105. Missing values within the LUT 235 may be generated using any desired interpolation technique.

In a second calibration mode, using the same color tiles, light properties from the inner sphere walls are also measured by the photometer 205. The measured light properties may be used to generate corresponding sphere data 215 that is provided to the computing device 135. This may be performed by flashing the xenon light 225 and measuring the light within the integrating-sphere spectrophotometer 100. The calibration logic 200 compares the measured sphere data 215 with the known values 205 for the current color tile sample 115 and generates a calibration offset value. A calibration look up table (LUT) 240 may be generated for the integrating-sphere spectrophotometer 100. Missing values may again be interpolated. In this manner, the camera 105 is color characterized in situ and may use the same color samples as used for the integrating-sphere spectrophotometer 100. Thus, the camera 105 is color-characterized in situ at a port of the integrating-sphere spectrophotometer 100. In alternate embodiments of the present invention, the color measuring system of FIG. 2 may switch between the two calibration modes for each different color sample 115 used.

During an initial characterization/calibration, a large set of samples may be used to calibrate the camera 105 and/or the integrating-sphere spectrophotometer 100. Subsequently, a smaller sample set may be used for daily calibration and/or calibration per use. Calibration may also be performed periodically to compensate, for example, for any camera color drift due to a change in temperature.

Although not shown, different light sources may be used for the integrating-sphere spectrophotometer 100 and for the camera 105. For example, the light source 110 may be positioned and used for measuring a gloss component by the camera 105. A different light source (not shown) may be positioned to provide diffuse illumination within the integrating-sphere spectrophotometer 100. By measuring diffuse light from the sample 115, the camera 105 is able to capture spatial variations in the color of the sample 115. Another light source (not shown) may then be provided as a high powered light that may be intermittently flashed. One example of such a light source is a Xenon lamp. In another embodiment, a light source (not shown) may be provided at a 45 degrees offset to the axis of the camera 105. The camera 105 is then able to simulate a 45/0 geometry of the sample 115.

In the various embodiments of the present invention described above implementing the image processing software 140, calibration logic 200 and the camera 105, the color measuring systems of the present invention are able to characterize colored areas in a multicolored sample, together with a combination of spectrophotometry and colorimetry of a large uniform standard made of the same reflecting material, to control the color in the multicolored sample and to make inferences about the spectrum of reflectance based on the color.

Figure 3:
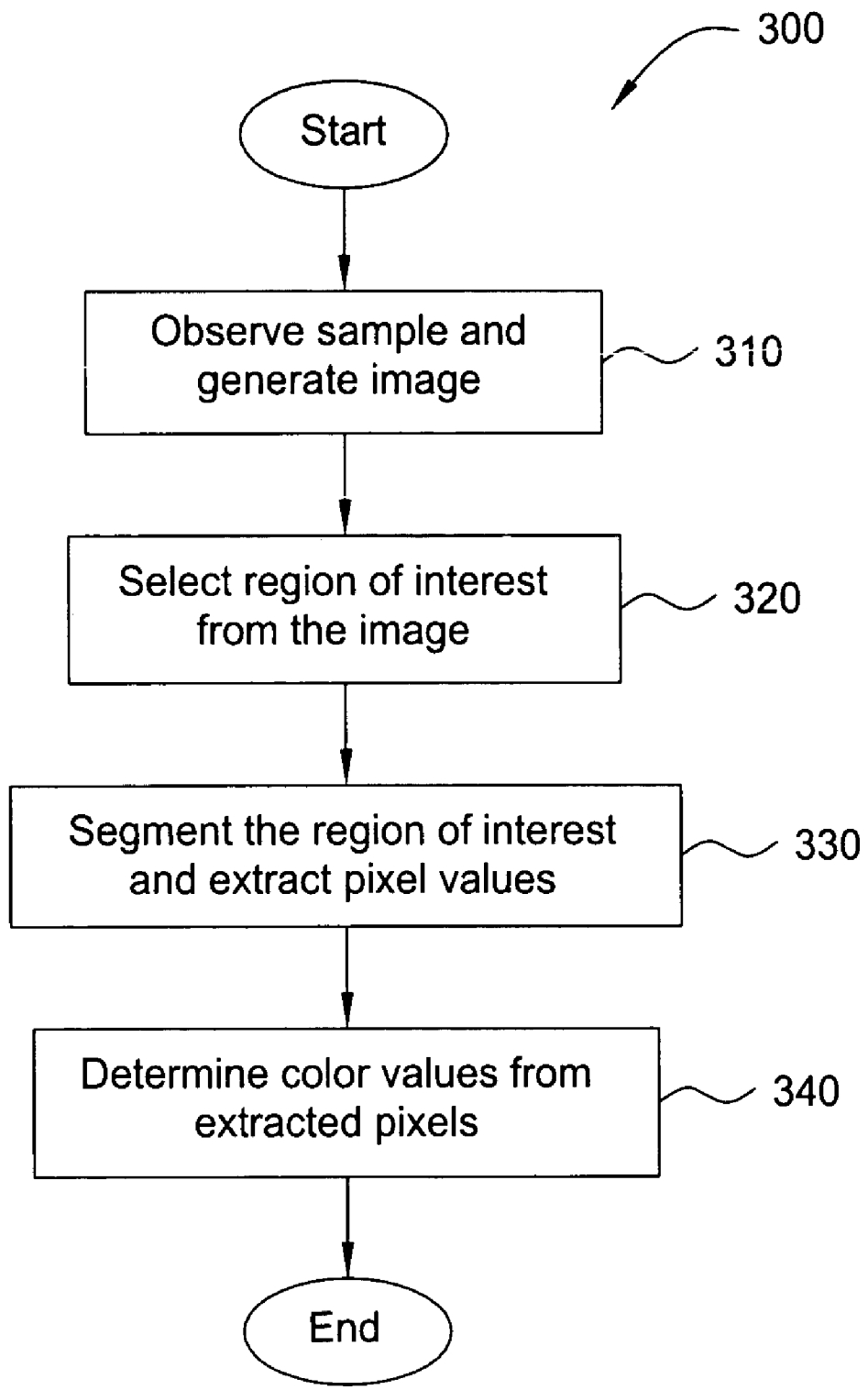
FIG. 3 depicts an embodiment of a method of the present invention for segmenting a region of interest from an image captured in accordance with an embodiment of the present invention.

FIG. 3 depicts an embodiment of a method of the present invention for segmenting a region of interest from an image captured in accordance with an embodiment of the present invention. While for purposes of simplicity of explanation, the method 300 of FIG. 3 is depicted and described as a series of blocks, it is to be appreciated that the methodologies are not limited by the order of the blocks, as some blocks may occur in different orders and/or concurrently with other blocks from that shown and described. It will be appreciated that the processes described in the series of blocks of the method 300 of FIG. 3 may be implemented using various programming approaches like machine language, procedural, object oriented and/or artificial intelligence techniques and the like.

The method 300 of FIG. 3 begins at step 310 by observing a sample with a color measuring device and generating an image from the measured sample. The method 300 proceeds to step 320.

At step 320, a region of interest, such as one or more pixels and/or an area within the image, is selected. The method 300 then proceeds to step 330.

At step 330, the region of interest selected in step 320 is segmented and pixel values from the region are extracted. The method 300 then proceeds to step 340.

At step 340, color values from extracted pixels are determined independently from other areas of the image. The method 300 is then exited.

In an alternate embodiment of the present invention, a method, such as the method 300 of FIG. 3, for segmenting a region of interest from an image captured in accordance with an embodiment of the present invention further comprises illuminating a test sample within an integrating sphere; measuring optical signals received from the test sample with a digital camera operably connected to the integrating sphere; and color-characterizing (or calibrating) the digital camera based on the optical the measured signals as compared to known signal values. In such an embodiment of the present invention, the digital camera may be operably connected to an included integrating sphere by being positioned at the location of a specular port or other port of the integrating sphere.

Figure 4:
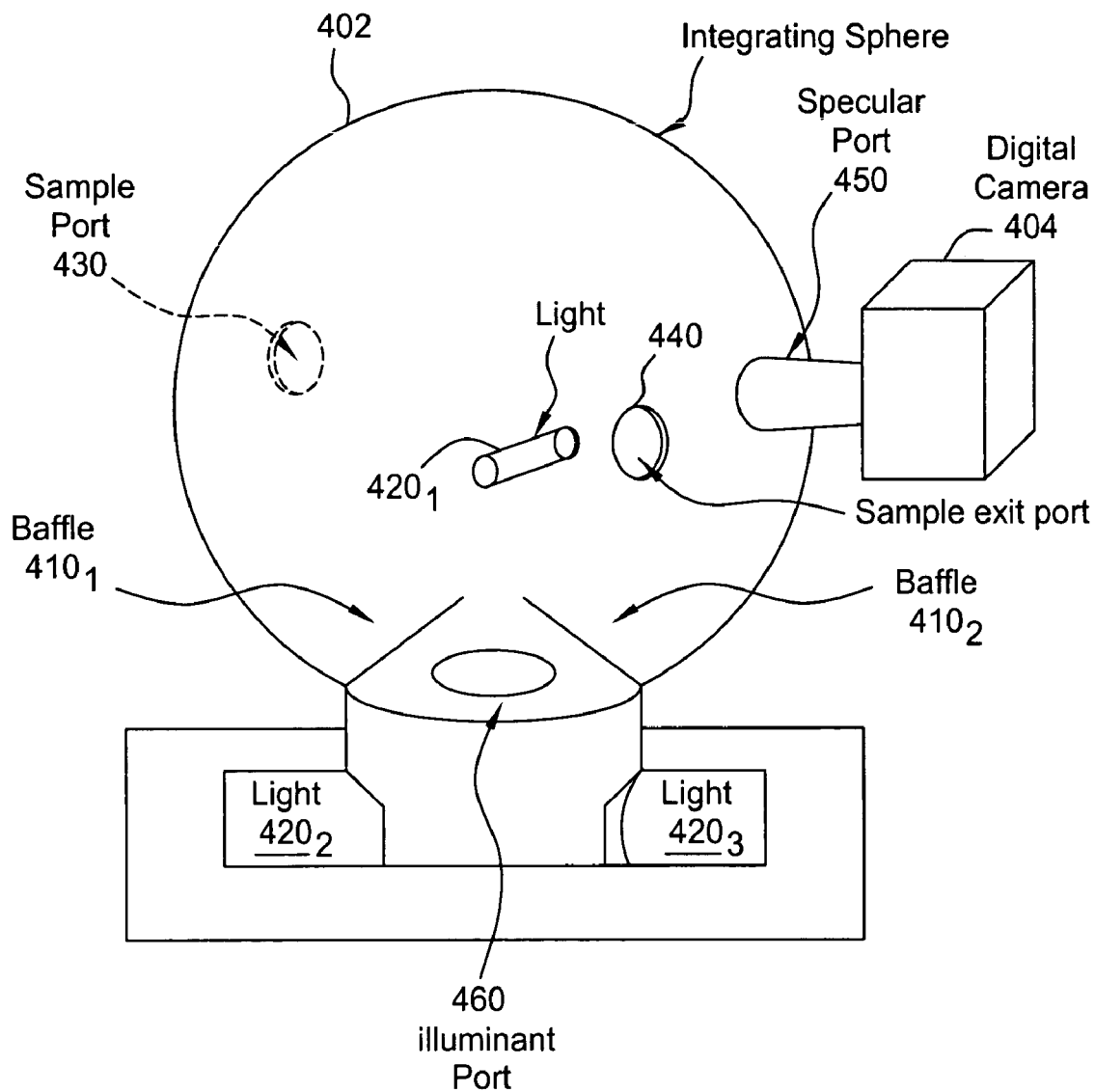
FIG. 4 depicts a three dimensional diagram of an integrating sphere and camera combination color measuring system in accordance with an alternate embodiment of the present invention.

FIG. 4 depicts a three dimensional diagram of an integrating-sphere spectrophotometer 402 and digital camera 404 combination color measuring system in accordance with an alternate embodiment of the present invention. In the color measuring system 400 of FIG. 4, the integrating-sphere spectrophotometer 402 illustratively comprises a variety of features such as two baffles $410_1$-$410_2$ (collectively baffles 410), three light sources $420_1$-$420_3$ (collectively light sources 420), and a plurality of ports, for example, a sample port 430, a sample exit port 440, a specular port 450, and an illuminant port 460.

The color measuring system 400 of FIG. 4 is configured such that the camera 404 is able to view a material sample-under-test through the open specular port 450 of the integrating-sphere spectrophotometer 402. That is, in the color measuring system 400 of FIG. 4, the first light source $420_1$ is positioned to illuminate a material sample using the illuminant port 460. This geometry allows the camera 404 to capture the image of the geometry of the specular (e.g. mirror-reflection) component of the light reflected from the material sample. The first light source $420_1$ is shielded from directly illuminating the camera, as the source $420_1$ lies outside of the integrating-sphere spectrophotometer 402 and is operably connected to the integrating-sphere spectrophotometer 402 by, for example, an opaque tube, or other light transferring/transmitting device that does not allow light to escape. The first light source $420_1$ is not flashed but turned on for several seconds to allow enough time for the camera to capture an image from the reflecting sample. The second light source $420_2$ is also not flashed and may be turned on and off independently of the first light source $420_1$. The second light source $420_2$, which may share an entry port with the third light source $420_3$, is shielded by the baffles 410 from directly illuminating the sample and from directly illuminating the specular port 450 and as such the digital camera 404.

A color measuring system of the present invention, such as the color measuring system 400 of FIG. 4, may be operated in various modes in accordance with the present invention. For example, a color measuring system of the present invention may be used as a normal spectrophotometer, to characterize the footprint of a specular reflection, to image a variegated sample, and to perform shape measurements of a three-dimensional sample. The example modes described herein are not to be interpreted as limiting in any way and more or less modes may be configured, used, and implemented as desired in accordance with the present invention.

In a normal spectrophotometer mode of a color measuring system of the present invention, and referring to FIG. 4, a sample is diffusely illuminated by the first light source $420_1$ (e.g., a Xenon flash lamp), and a photometer (not depicted in FIG. 4) is mounted in or operably connected to the sample exit port 440. The photometer at the sample exit port 440 collects the reflected light from the sample and analyzes it into narrow-band wavelength components. The photometer may include photodiodes, photodetectors, or other type of optical radiation detecting device. The digital camera 404 is not used in the normal spectrophotometer operating mode. The specular port 450 may be either open or closed for the measurements made in this mode.

In a second mode of operation, a color measuring system of the present invention may be used to characterize the specular-reflected component of a material in the sample port 430 of the integrating-sphere spectrophotometer 402 of the color measuring system of FIG. 4. In this embodiment, the digital camera 404, installed at the open specular port 450 (which is aimed at the sample), is used to separate the specular from the matte component of reflection of the light from the material illuminated by the second light source 420$_2$ through image processing among the color channels of the camera. For highly chromatic samples, the image processing assigns a pixel as belonging to the specular component if the pixel's ratios of red-to-green, green-to-blue, and red-to-blue are sufficiently close to the corresponding ratios for the incident illumination. For samples that do not display sufficient spectral differences between specular and matte components, a pixel is assigned specular status on the basis of its intensity, I, compared with the intensity, $I_m$, of the mirror-path pixel and compared with the intensity, $I_o$, of a pixel that is far from the mirror-path pixel.

The intensity is a linear combination (with positive coefficients) of red, green, and blue channels from the digital camera. For example, a pixel with intensity I (as composed by a positive linear combination of red, green, and blue channels) is assigned "specular" status if $(I-I_o)/(I_m-I_o)$ is greater than a certain constant b that is between 0 and 1. For example, a reasonable value for b is ½. Logic may be configured to determine the optimum size of a specular port for a particular kind of reflecting sample. Alternatively, if the camera is sufficiently well calibrated, the color measuring system of FIG. 4, as described directly above, may be used as a direct reading device that may be used to separate the specular from the matte components of reflection without recourse to multiple measurements of the sample.

In a third mode of operation, a color measuring system of the present invention, and specifically referring to the color measuring system 400 of FIG. 4, may be used to image a variegated sample. In this mode of operation, the digital camera 404 is used in conjunction with the third light source 420$_3$ to provide calorimetric data on small subsections of the image of a non-uniform sample. That is, the image captured by the digital camera 404 is communicated to a computer (not shown), such as the computing device 135 of FIGS. 1 and 2, where logic is configured to automatically segment the image into uniformly colored areas, each of which may be separately characterized as a respective color.

In a fourth mode of operation, a color measuring system of the present may be used to perform shape measurement of a three-dimensional sample. For example, a shape measurement may be performed with the digital camera 404 by replacing one of the light sources (e.g. the light source 110 in FIG. 1 or the second light source 420$_2$ in FIG. 4) by a projector that projects a rectangular grid onto a sample. The camera image of the grid conveys the three-dimensional shape of the object, which would otherwise be inaccessible to the camera 404. In such an embodiment of the present invention, the projector and the digital camera 404 are configured to together triangulate the position of a grid point, an action directly analogous to two cameras looking at the same point in space, except the second camera is sending instead of receiving light. The technology of such projection, called rasterstereography, has been used in photogrammetry, for example, and with medical-imaging applications and with industrial inspections. Configuring a color measuring system of the present invention as described above enables the system to perform texture analysis on a non-smooth sample and determine physical properties of the sample (e.g. 3-D characteristics, depth, direction of grain, and the like).

The various modes described above may also have various interactions. For example, for either the second or third operating modes described above, the system may be further configured to classify the texture of a material sample using the collected light samples and computer algorithms. In addition, for either the second or third operating modes, the image-segmentation logic associated with the camera may also be used to determine the state of the opening of the sample port, the aperture of the port, and the position of the sample (described in greater detail below). It should be noted that a color measuring system of the present invention may switch between its various modes of operation by turning on and off the various included light sources. That is, if an embodiment of a color measuring system of the present invention includes all of the light sources necessary to perform its various function and modes of operation, the system may vary between its modes of operation by implementing one or more or a combination of one or more of the included light sources.

As previously described, a color measuring system of the present invention is able to programmatically determine an aperture size of a sample port of a color measuring system of the present invention, and/or determine if the sample port is open or closed. More specifically, a color measuring system of the present invention comprising an integrating sphere may include a digital camera operably connected to a port of the integrating sphere. The digital camera is configured to generate an image from light signals measured from a sample positioned in a sample port. The color measuring system may include logic configured to determine a size of the aperture of the sample port using the image from the digital camera. For example, using the image of the sample, the logic determines an area of the camera receiving color from the sample and what areas are not by performing pixel analysis. The area where color is located is then used to determine the size of the aperture. In this manner, the color measuring system can automatically determine the aperture size without using sensors, detectors, and other mechanisms. The same technique may be used to automatically determine if the sample port of the integrating sphere is opened or closed.

Furthermore, a comparison of the outputs of the first and third operating modes described above may be associated to provide a correspondence or determine a relationship between the reflectance spectrum of a standard patch for a colorant (the first operating mode) and a batch application of the colorant in a non-uniform pattern (the third operating mode). Even further, a training sample set, comprising spatially uniform samples of known spectral reflectance, may be used to calibrate/characterize both the integrating sphere and the digital camera.

As described above, a set of material samples with known spectral reflectances may be used to calibrate a color measuring system of the present invention, and may also be used to color-characterize the digital camera. Color characterization of the digital camera involves determining the input colors that correspond to the output digital values from the camera. Many different known methods and techniques may be used to calibrate the camera. For example, a lookup table having offset values may be generated for a set of test samples and other values determined using interpolation techniques.

In one embodiment of the present invention, methodologies are implemented as processor executable instructions and/or operations provided on a computer-readable medium. Thus, in one example, a computer-readable medium may store and/or communicate processor executable instructions operable to perform any of the methodologies, functions, actions, and/or their equivalents described herein. One form of computer-readable medium may include a carrier wave that can transmit a set of processor executable instructions over a network.

Figure 5:
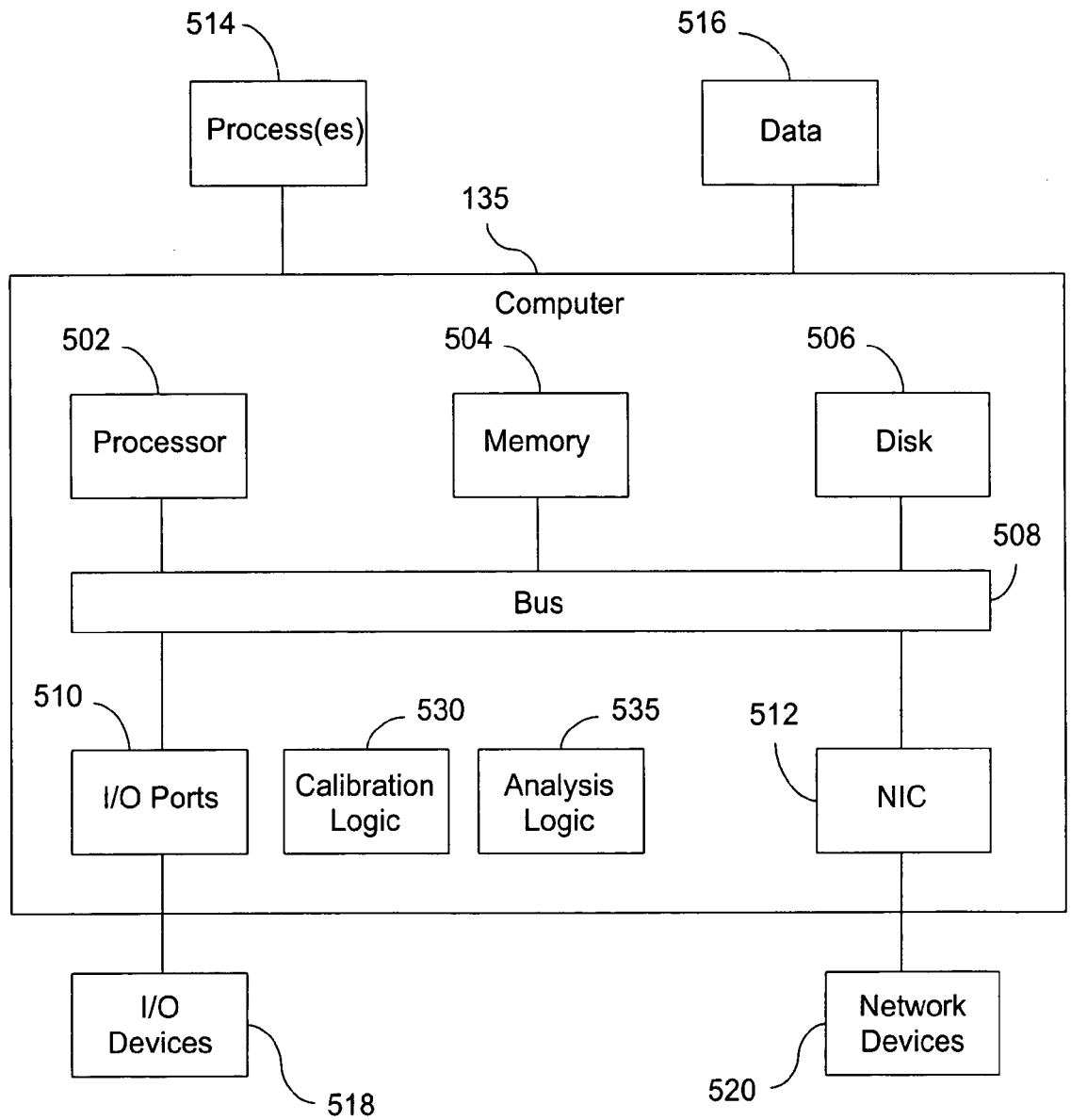
FIG. 5 depicts a high level block diagram of a computing device suitable for use in the color measuring systems of FIGS. 1, 2 and 4 for performing the methods and operations of the present invention in accordance with an embodiment of the present invention.

FIG. 5 depicts a high level block diagram of a computing device suitable for use in the color measuring systems of FIGS. 1, 2 and 4 for performing the methods and operations of the present invention in accordance with an embodiment of the present invention. The computing device 135 of FIG. 5 illustratively comprises a processor 502, a memory 504, and input/output ports 510 operably connected by a bus 508. The computing device 135 may be operably connected to any color measuring system, spectrophotometer, integrating-sphere, and the like, described herein to provide, for example, data processing functions and storage of information. Executable components of logics and programs described herein may be stored in and executed by the computing device 135 of FIG. 5. It will be appreciated by those skilled in the art and informed by the teachings of the present invention that other computer devices may also be employed with the various embodiments of the systems and methods of the present invention described herein.

In one embodiment of the present invention, the computing device 135 may further include a calibration logic 730 that is configured to perform calibration functions for a color measuring device and camera. The calibration logic 730 may be the calibration logic 200 described in FIG. 2 and may include the same or similar components. The computing device 135 may also include an analysis logic 735 configured to analyze image data measured from a color measuring device/camera combination. The analysis logic 734 may be the analysis logic 140 described in FIG. 1 and may include the same or similar components. The calibration logic 730 and the analysis logic 735 may be embodied as processor executable instructions that can cause the computing device 135 to perform desired functions, actions, and/or to behave in a desired manner.

The processor 702 may be a variety of various processors including dual microprocessor, other multi-processor architectures, an ASIC, or other type of logic configured to process instructions. The memory 704 may include volatile memory and/or non-volatile memory. The non-volatile memory can include, but is not limited to, read only memory (ROM), programmable read only memory (PROM), electrically programmable read only memory (EPROM), electrically erasable programmable read only memory (EEPROM), and the like. Volatile memory can include, for example, random access memory (RAM), synchronous RAM (SRAM), dynamic RAM (DRAM), synchronous DRAM (SDRAM), double data rate SDRAM (DDR SDRAM), and direct RAM bus RAM (DRRAM).

In addition, a disk 706 may be operably connected to the computing device 135 via, for example, an input/output interface (e.g., card, device) 718 and an input/output port 710. The disk 706 may include, but is not limited to, devices like a magnetic disk drive, a solid state disk drive, a floppy disk drive, a tape drive, a Zip drive, a flash memory card, and/or a memory stick. Furthermore, the disk 706 may include optical drives like a compact disc ROM (CD-ROM), a CD recordable drive (CD-R drive), a CD rewriteable drive (CD-RW drive), and/or a digital video ROM drive (DVD ROM). The memory 704 is able to store executable/executing processes 714 and/or data 716, for example. The disk 706 and/or memory 704 are able to store an operating system that controls and allocates resources of the computing device 135.

The bus 708 of the computing device 135 of FIG. 5 may comprise a single internal bus interconnect architecture and/or other bus or mesh architectures. The bus 708 may be of a variety of types including, but not limited to, a memory bus or memory controller, a peripheral bus or external bus, a crossbar switch, and/or a local bus. The local bus may be of varieties including, but not limited to, an industrial standard architecture (ISA) bus, a microchannel architecture (MSA) bus, an extended ISA (EISA) bus, a peripheral component interconnect (PCI) bus, a universal serial (USB) bus, and a small computer systems interface (SCSI) bus.

The computing device 135 of the present invention may interact with input/output devices 718 via i/o interfaces and input/output ports 710. Input/output devices 718 may include, but are not limited to, a keyboard, a microphone, a pointing and selection device, cameras, video cards, displays, disk 706, network devices 720, and the like. The input/output ports 710 may include but are not limited to, serial ports, parallel ports, and USB ports.

The computing device 135 may operate in a network environment and thus may be connected to a color measuring device and to network devices 720 via the i/o devices 718, a network interface card 712, and/or the i/o ports 710. Through the network devices 720, the computing device 135 may interact with a network. Through the network, the computing device 135 may be logically connected to remote computers. The networks with which the computing device 135 may interact include, but are not limited to, a local area network (LAN), a wide area network (WAN), and other networks. The network devices 720 may connect to LAN technologies including, but not limited to, fiber distributed data interface (FDDI), copper distributed data interface (CDDI), Ethernet/IEEE 802.3, token ring/IEEE 802.5, wireless/IEEE 802.11, Bluetooth, and the like. Similarly, the network devices 720 may connect to WAN technologies including, but not limited to, point to point links, circuit switching networks like integrated services digital networks (ISDN), packet switching networks, and digital subscriber lines (DSL). Any of these communication connections may also be used to operably connect a color measuring device to the computing device 135.

While the forgoing is directed to various embodiments of the present invention, other and further embodiments of the invention may be devised without departing from the basic scope thereof. As such, the appropriate scope of the invention is to be determined according to the claims, which follow.

What is claimed is:
1. A method for color measuring, comprising:
   collecting light signals from an illuminated sample using a multi-segmented detector configured to capture spatial variations in a color of the sample;
   dividing a total signal received by said detector into groups of one or more of said segments, said groups representing different spatial regions of said illuminated sample; and
   measuring color information for one or more of said divided groups independently of a remainder of said divided groups, in order to produce a color measurement for said one or more of said divided groups.

2. The method of claim 1, wherein said multi-segmented detector comprises a digital camera.

3. The method of claim 2, wherein said segments comprise pixels.

4. The method of claim 1, wherein said groups are formed by segments receiving signals having similar color properties.

5. The method of claim 1, further comprising color-characterizing said multi-segmented detector with standard test samples.

6. An apparatus for color measuring, comprising:
a spectrophotometer;
at least one light source for illuminating an interior of the spectrophotometer and at least one sample; and
a multi-segmented detector configured at a port of the spectrophotometer and being adapted to measure light components from said at least one sample and to capture spatial variations in the color of the sample.

7. The apparatus of claim 6, wherein said spectrophotometer comprises an integrating-sphere.

8. The apparatus of claim 6, wherein said multi-segmented detector comprises a digital camera.

9. The Apparatus of claim 6, wherein one of said at least one light sources is configured to directly illuminate the at least one sample, and the at least one sample and the multi-segmented detector are apposed to a direction of the light from said one of said at least one light source to form a specular path connecting the light, the sample, and the multi-segmented detector.

10. The apparatus in claim 6, wherein one of said at least one light sources is configured to diffusely illuminate the sample.

11. An apparatus for color measuring, comprising:
a spectrophotometer;
at least one light source for illuminating an interior of the spectrophotometer and at least one sample;
a multi-segmented detector configured at a part of the spectrophotometer and being adapted to measure light components from said at least one sample; and
at least one photometer for measuring light components from standard test samples for use in color-characterizing at least one of said multi-segmented detector and said spectrophotometer.

12. An apparatus for color measuring, comprising:
a spectrophotometer;
at least one light source for illuminating an interior of the spectrophotometer and at least one sample; and
a multi-segmented detector configured at a port of the spectrophotometer and being adapted to measure light components from said at least one sample,
wherein one of said at least one light sources is configured to directly illuminate the at least one sample, and the at least one sample and the multi-segmented detector are opposed to a direction of the light from said one of said at least one light source to form a specular path connecting the light, the sample, and the multi-segmented detector,
and wherein said one of said at least one light sources comprises a light projector that projects an illuminated grid image onto the sample which is captured by the multi-segmented detector.

13. The apparatus of claim 12, wherein said captured illuminated grid image is used to determine if a sample port of said spectrophotometer is opened or closed, and if open, the size of the opening.

14. A computer-readable medium configured to provide processor executable instructions operable to perform a method, the method comprising:
illuminating a test sample within an integrating sphere;
measuring optical signals received from the test sample; and
color-characterizing a multi-segmented detector configured for capturing spatial variations in a color of the test sample, based on the optical signals received where the multi-segmented detector is operably connected to the integrating sphere.

15. A computer-readable medium configured to provide processor executable instructions operable to perform a method, the method comprising:
receiving an image generated by a multi-segmented detector from measured light signals from a color sample, the multi-segmented detector being configured to capture spatial variations in a color of the sample;
selecting a region of interest from within the image; and
measuring color information for the selected region of interest independently from other areas of the image, in order to produce a color measurement for the selected region of interest.

16. The computer-readable medium of claim 15 where the processor executable instructions are embodied as a graphical user interface.

17. A color measuring system, comprising:
a spectrophotometer for providing and directing light signals from a sample;
at least one light source for illuminating an interior of said spectrophotometer and said sample; and
a multi-segmented detector configured in a port of the spectrophotometer and being configured to measure the light signals from the sample and to capture spatial variations in the color of the sample;
selection logic configured to enable a region of interest to be selected from the measured light signals; and
analysis logic adapted to determine color information from the region of interest separately from other measured light signals.

18. The color measuring system of claim 17, further comprising:
calibration logic configured to calibrate or characterize the multi-segmented detector using the measured light signals and known color values for the sample.

19. The color measuring system of claim 17, wherein said multi-segmented detector is adapted to measure optical radiation from the sample and generate image data of the sample and to communicate the image data to a computing device using wireless communication.

20. A color measuring system, comprising:
a spectrophotometer for providing and directing light signals from a sample;
at least one light source for illuminating an interior of said spectrophotometer and said sample;
a multi-segmented detector configured in a port of the spectrophotometer and being configured to measure the light signals from the sample;
selection logic configured to enable a region of interest to be selected from the measured light signals;
analysis logic adapted to determine color information from the region of interest separately from other measured light signals; and
logic configured to determine a size of an aperture of a sample port using the measured light signals from the multi-segmented detector.

21. A color measuring system, comprising:
- a spectrophotometer for providing and directing light signals from a sample;
- at least one light source for illuminating an interior of said spectrophotometer and said sample;
- a multi-segmented detector configured in a port of the spectrophotometer and being configured to measure the light signals from the sample;
- selection logic configured to enable a region of interest to be selected from the measured light signals; and
- analysis logic adapted to determine color information from the region of interest separately from other measured light signals,
- wherein said color measuring system comprises a plurality of modes of operation including at least a spectrophotometer mode, a mode used to characterize the specular-reflected component of a material, a mode used to image a variegated sample and a mode used to perform shape measurement of a three-dimensional sample.

22. The color measuring system of claim 21, wherein said at least one light source comprises at least two light sources and a light projector that projects an illuminated grid image onto the sample and wherein said color measuring system switches between modes of operation by activating and deactivating specific ones of said light sources.

* * * * *